United States Patent [19]
Ahlqvist

[11] Patent Number: 5,312,758
[45] Date of Patent: May 17, 1994

[54] METHOD AND DEVICE FOR COMBINED ENRICHMENT, PROCESSING AND EMBEDDING OF CYTOLOGICAL SPECIMENS ACCORDING TO HISTOLOGICAL PRINCIPLES

[75] Inventor: Johan E. W. Ahlqvist, Helsinki, Finland

[73] Assignee: Oy Sed-Par-Sed Ab, Finland

[21] Appl. No.: 838,310

[22] PCT Filed: Sep. 5, 1990

[86] PCT No.: PCT/FI90/00209

§ 371 Date: May 4, 1992

§ 102(e) Date: May 4, 1992

[87] PCT Pub. No.: WO91/03720

PCT Pub. Date: Mar. 21, 1991

[30] Foreign Application Priority Data

Sep. 8, 1989 [FI] Finland ............................ 894244

[51] Int. Cl.$^5$ .................. G01N 33/48; G01N 1/00
[52] U.S. Cl. ....................... 436/63; 435/284; 435/287; 436/174; 436/176
[58] Field of Search .............. 422/99, 102, 104; 436/63, 174, 176; 435/284, 287

[56] References Cited

U.S. PATENT DOCUMENTS

| | | | |
|---|---|---|---|
| 2,996,762 | 8/1961 | McCormick | 264/238 |
| 3,411,185 | 11/1968 | Pickett | 425/117 |
| 3,456,300 | 7/1969 | Pickett | 425/117 |
| 3,982,862 | 9/1976 | Pickett et al. | 425/117 |
| 4,363,783 | 12/1982 | Sitte | 422/68 |
| 4,557,903 | 12/1985 | McCormick | 422/101 |
| 4,569,647 | 2/1986 | McCormick | 425/117 |
| 4,734,372 | 3/1988 | Rotman | 435/291 |
| 4,801,553 | 1/1989 | Owen et al. | 436/174 |

Primary Examiner—James C. Housel
Assistant Examiner—Robert Carpenter
Attorney, Agent, or Firm—Wolf, Greenfield & Sacks

[57] ABSTRACT

A method and device for the processing of cytological specimens. The device comprises a preferably cone-shaped receptacle with a closed bottom part, sidewalls defining an upper aperture with a surface area larger than that of the bottom part, and a perforated membrane adapted to cover the aperture of the receptacle for retaining the cytological specimens. The membrane is preferably a mesh having a mesh size of up to 80 microns, the hydraulic conductance of the membrane being sufficient to allow the exchange of processing fluids when the receptacle is inserted into a tissue processing apparatus. The sidewalls form an obtuse angle with the bottom in order to promote such an exchange. In the method, the receptacle with specimens is inserted into a tissue processor with the membrane in a vertical position. After processing and paraffination, the receptacle is cooled allowing the specimens to sedimentate to form an enriched layer at the bottom of the receptacle. The solid paraffin block with enriched layer is thereafter removed from the receptacle and cut on a microtome.

11 Claims, 1 Drawing Sheet

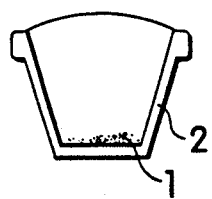 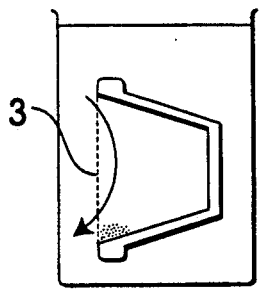 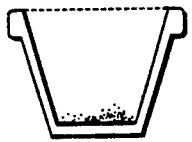 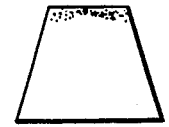
Fig. 1A  Fig. 1B  Fig. 1C  Fig. 1D
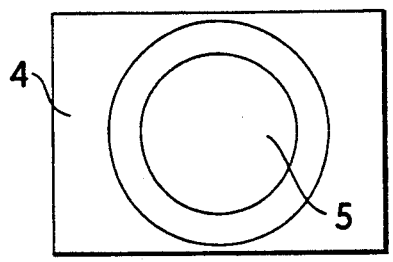
Fig. 2B
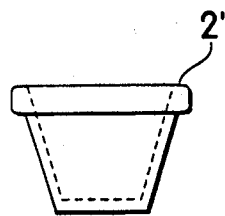 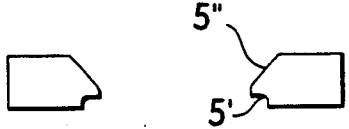 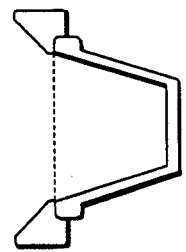
Fig. 2A  Fig. 2C  Fig. 2E
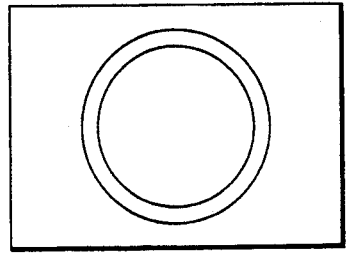
Fig. 2D

METHOD AND DEVICE FOR COMBINED ENRICHMENT, PROCESSING AND EMBEDDING OF CYTOLOGICAL SPECIMENS ACCORDING TO HISTOLOGICAL PRINCIPLES

BACKGROUND OF THE INVENTION

The present invention relates to the combined enrichment, processing and embedding of cytological specimens according to histological principles.

Most neoplastic and many other diseases are diagnosed by microscopic examination of cytological cell or of histological tissue specimens. New methods for obtaining cytological specimens from tissues, e.g., by aspiration using fine needles and by brushing material off mucosal membranes, have increased the demand for cytological methods that permit diagnostic accuracy comparable to that of histological specimens. Cytological and histological preparations should be thin enough to let pass the incident light of the microscope after staining and they should permit the use of all histochemical and immunological staining methods that are essential for accurate diagnoses.

Cytological specimens can be smeared onto slides and this originally haematological technique is used also for secretions and fine needle aspiration biopsies. Cells in fluids can be enriched onto filters (e.g. Millipore filters, Millipore Corporation, Bedford, Mass.) that permit the fluid proper to pass; in this technique the number of applicable staining methods is limited because the filters absorb many dyes. Cells can be centrifuged onto glass slides. Disadvantages common to these techniques are that specimens may contain cell clusters so large that they cannot be analysed since enough light does not pass them after staining and, furthermore, clusters of cells cannot easily be divided for staining by special techniques.

The above draw-backs do not apply to histological techniques and some prefer to concentrate and collect valuable cytological specimens to bodies that can be processed and embedded histologically. Fluid gelatin, agar, gels and plasma have been used as "glues" that can be solidified to form bodies that can be processed histologically. Cell clusters have been collected into funnels prepared from filter paper or plastic (Nordgren Hans, not published) nets, or onto polycarbonate filters (Nordgren et al. APMIS 97:136-42, 1989) that can be processed histologically. Fixed, repeatedly centrifuged and acetone-dehydrated specimens have been paraffinized after evaporation of the acetone, concentration of the specimen being obtained by centrifugation in the melted paraffin, but the method is not suitable to mucinous specimens (Krogerus & Anderssson. Acta Cytol 32: 585-7, 1988) and seems laborious.

Histological tissue specimens, after fixation, are transferred through a series of processing fluids that dehydrate and clear the tissues before they are impregnated by melted paraffin that upon cooling hardens to a block that is cut by a microtome, the thin sections after staining being examined microscopically. The tissue pieces are generally transferred to small perforated and labelled tissue casettes, which during processing are kept in large perforated baskets. After paraffination, the tissue pieces are transferred manually to metal molds for embedding, the molds being covered by the inverted labelled casette bottoms that after hardening of the paraffin remain attached to the paraffin block, the casette being clamped to the microtome jaws for cutting.

The latter laborious step of embedding has been considerably simplified by Pickett et al (U.S. Pat. No. 3,982,862). These authors transfer the fixed tissue piece directly into an open base pan, serving both as part of a tissue "casette" during paraffination and, after completed paraffination, as an embedding mold. For processing, the base pan is closed by a perforated and labelled top member that, after processing in a manner similar to the casette bottoms above, remains attached to the paraffin block and fits the jaws of a microtome. Adequate paraffination is achieved when, during processing, the top member closing the base pan is positioned vertically. However, the method by Pickett et al. is as unsuitable for cytological specimens as are conventional histological techniques.

In conventional automatic tissue processor types the baskets holding the casettes are lifted into the air when transferred from one processing fluid to the next one. In some modern processor types the baskets are kept in one single closed compartment in which the fluids are exchanged, periods of low pressure being applied to speed up paraffination.

The technical disadvantages of cytological techniques were mentioned above. From a cytological point of view the main disadvantages of histological techniques are that nucleated cells (diameter range some 10-20 $\mu$m) and small cell clusters easily escape through histological casette perforations (>1000 $\mu$m) and that specimens are not adequately enriched unless they are "glued" into pieces corresponding in size to histological tissue ones.

SUMMARY OF THE INVENTION

The present invention describes a device and a method by which the aforementioned disadvantages may be eliminated and by which cytological specimens, in a manner that involves no rough handling of fragile fragments, simultaneously are enriched and impregnated with paraffin to form paraffin blocks that can be sectioned also serially, permitting the use of all the histochemical and immunological methods that often are of key importance for the diagnosis of human diseases.

The method according to the invention for processing cytological specimens is characterized in that it comprises inserting the specimens to be processed into a cup-shaped receptacle having a closed bottom part, closed side-walls the upper edge of which define an upper aperture in the receptacle having an area larger than the area of the bottom part, the side-walls forming an obtuse angle with the said bottom part, the aperture is covered with a perforated membrane retaining the cytological specimens while still exhibiting a hydraulic conductance high enough as to allow the exchange of processing fluids therethrough, the receptacle with specimens is introduced in a tissue processing apparatus with the perforated membrane in the vertical position, after processing the receptacle is turned so that the perforated membrane is in the horizontal position and directed upwards, thus permitting the enrichment of the specimens by sedimentation to form an enriched layer at the receptacle bottom, and after hardening, the paraffin block formed is removed from the receptacle for histological examination.

Though terms such as "paraffination" and "paraffin block" have and will be used, the invention is not restricted to the use of paraffin wax proper but covers the use of also other substances with properties suitable for histological studies.

The perforated membrane covering said processing receptacle or cup and preventing the specimen from escaping, in addition to being able to withstand moderate mechanical damage optimally should have perforations small enough to prevent small single nucleated cells (about 10 μm) from escaping but a hydraulic conductance high enough to permit proper exchange of processing fluids when other conditions, notably the shape of the receptacle, favour such exchange. The fact that fluid flow rather than diffusion is responsible for exchange of processing fluids in automatic tissue processors is indicated, e.g., by that fluid exchange through a membrane is very poor in a cup filled with fluid, closed by a perforated membrane and submerged vertically (membrane horizontal) with the opening directed upwards in a larger vessel containing fluid with the same or lower density, and far too poor to provide adequate paraffination.

The amount of fluid flow $Q_{fluid}$ through a membrane with cylindrical perforations obeys Poiseuille's law, depending on the pressure difference ($P_1$-$P_2$) across the net and the hydraulic conductance per unit area of the membrane or $$Q_{fluid} = (P_1 - P_2) \times \frac{N \times \pi \times r^4}{8 \times \text{visc.} \times l}$$

from which follows that flow through a perforated membrane can be increased by increasing the number N of perforations per unit area, to the fourth power by increasing the perforation radius r, by decreasing the viscosity (visc.) of the fluid and by decreasing the length l of the perforations and by increasing the pressure difference. The radius of the perforations of commercially available histological perforated membranes (U.S. Pat. No. 3,982,862) and processing casettes ($\geq 500$ μm) is long compared to that of a perforated membrane, which holds back nucleated cells (radius about 5 μm), but the latter's low hydraulic conductance due to the short perforation radius must be compensated for by a vast number of perforations per unit area, the use of a thin membrane and factors that increase the filtration pressure resulting in flow. The use of filters employed in cytology (e.g. Millipore Corporation, Bedford, Mass., U.S.A) was considered but these filters are too fragile for the purpose of the invention. Nylon nets with mesh sizes ranging from 7 to 5000 μm are commercially manufactured (Zuricher Beuteltuschfabrik Ag, Ruschlikon, Switzerland). Using the cups to be described below, poor paraffination was regularly obtained with the nets less than 10 μm (opening size 10×10 μm), whereas adequate paraffination regularly was obtained with the 20 μm net. Thus, depending on specimen type, a mesh size from 10 μm up, e g. up to 80 μm is contemplated in accordance with the invention, good results being obtained with nets 15 to 35 μm, a 20 μm net being optimal from several points of view. It is however conceivable to use the finer type nets if processing is enhanced, e.g. by employing vacuum in the new automatic tissue processor types.

Under otherwise similar conditions, the hydraulic conductance of a "histological" perforation with a radius of 500 μm (e.g., U.S. Pat. No. 3,982,862) is about $3.9 \times 10^6$ higher than that of one with a radius calculated from the surface area (400 μm) of the mesh (20×20 μm) in the above 20 μm net. This is, however, in part compensated for by other properties of the above nylon net, such as its open surface area of 16%, the about 40000 perforations/cm$^2$ (to be compared to U.S. Pat. No. 3,982,862: open surface area 6.37% and 8.1 perforations/cm$^2$) and a fabric thickness of only 60 μm.

Though the properties of a net of the above described type made the method of the invention possible, the invention is not restricted to the use of that type of net or the indicated mesh-size and it covers also the use of fragile cytological filters supported by tougher widemeshed nets and other fabrics having properties corresponding to these nets. The perforated membrane will henceforth be termed net.

The invention also concerns a device or receptacle for the processing of cytological specimens which comprises a cup with a closed bottom part, closed side-walls defining an upper aperture with a surface area larger than that of the said bottom part, the side-walls forming an obtuse angle with the bottom part, as well as a perforated membrane adapted to cover the aperture of the cup for retaining the cytological specimens, the hydraulic conductance of the membrane being high enough as to allow the exchange of processing fluids through the membrane when the cup is inserted in the tissue processing apparatus, the shape of the cup promoting such exchange, and means for attaching the said membrane to the cup.

The cup according to the invention can have a square (inverted frustrum of a pyramid) or rectangular cross-section but to facilitate the removal of the hardened paraffin, a cup with a frustoconical shape is preferable, the net covering the said upper open larger base of the cone. An essential characteristic is, however, that the angle between the closed bottom and the side-walls should be obtuse, and preferably wider than about 105° and preferably not larger than appr. 135°. A wide angle is essential because when the cup is covered with the said net and the net is in the vertical position, fluid exchange is rather sluggish if the shape of the cup is cylindrical (angle between bottom and sidewalls 90°) and if it is deep. In conventional tissue processor types we have also experienced poor paraffination in cups in which the said angle is 100° but never with angles >105°. Good paraffination is generally always obtained with angles between 105° and 120°. The wider the angle the better is the fluid exchange. The fluid exchange is, according to tests performed, also driven by the hydrostatic pressure created by differences in fluid density on both sides of the perforated net and by the movement of the baskets in conventional automatic tissue processors. In the latter, fluid does not flow out through the nets when netted cups are lifted into the air while being transferred from one processing fluid to the next one; fluid does, however, flow out of cups half-filled with fluid if the net above the fluid level is dry, indicating that the surface tension of the fluid in a wetted net prevents the hydrostatic pressure at the lower margin of the net from leading to flow through the net. In those automatic tissue processors in which periods of vacuum are employed, fluid exchange is enhanced by vaporization of fluids; bubbles forming behind the net do not pass it, apparently due to the surface tension in the net, and the cups seem to empty; when the vacuum is relieved the cups refill with fluid. Though this enhances fluid exchange, tests performed indicate that this does not suffice to ensure adequate paraffination if the cups are kept upright (nets horizontal) but when the nets are vertical adequate paraffination is obtained even with short (1 hour) paraffination schedules.

The small bottom area of the cup also provides for the final enrichment of the specimen in melted paraffin due to the fact that cells and fragments sedimentate from a comparatively large volume of fluid to a comparatively small bottom area. Tests have also shown that too wide an angle between the bottom and the sidewalls, i.e. above appr. 135°, prevents cells and fragments from gliding along the sidewalls to the bottom. Larger angles could be considered if the cup with specimens is centrifuged.

The cup according to the invention serves both as a processing receptacle and an embedding mold, in this respect resembling the base-pan according to the U.S. Pat. No. 3,982,862, but in contrast to the present invention, the specimen is not enriched to a small section area in the known technique. Base pans with an 92°–100° angle between the bottom and the side-walls have been proposed in that patent but solely for the easy removal of the paraffin block. If used together with the above 20 μm mesh size net those angles would probably result in poor paraffination of many specimens.

According to one preferred embodiment the said net can be clamped to the open aperture of the said cup by a closing ring, secured to the cup by pincers, springs or similar devices which grip ridges or horizontal bars on the cup.

Preferably the net can be incorporated to cover an opening in a separate body or socket, the opening corresponding in size to the inner periphery of the upper aperture of the cup and provided with a groove surrounding the net that mates the outer periphery of the upper aperture of the cup, preventing the socket and the net from sliding away from the upper aperture of the cup.

According to a preferred embodiment, in both closing rings and the netted bodies or sockets, henceforth termed net-pieces, the side-walls of the opening extending above the nets form an angle with the surface of the net wider than the angle between the bottom of the cup and its side-walls, in order to enhance that down- or uphill exchange of processing fluids through the net that also determines the angle between the bottom and the side-walls of the cups. The net-piece is preferably made of material resistant to the processing fluids, having at least one surface that can be labelled, thus forming a body that by a separate spring or pincers can be secured to ridges or bars on the cup. When the paraffin has hardened to a solid block, the net-piece with attached paraffin block is removed from the cup, the outer dimensions of the net-piece fitting the jaws of a microtome.

The cup according to the invention should preferably stand firmly while the specimen is introduced into it and during embedding. This can be achieved by using a cup-holder resting on a table surface and provided with a hole corresponding in shape to the outer dimensions of the lower part of the cup. To enhance conductance of heat to the cup while the specimen is enriched during embedding the cup-holder preferably is made of metal. To prevent a conical cup from moving when the hardened paraffin block with attached net-piece is removed with a twisting movement from the cup, after gentle warming of the combined device in warm tap water, the lower outer edge of the cup is preferably provided with short horizontal bars that fit peripheral slits in the conical hole of the cup-holder.

The said springs or pincers used to secure the net-piece to the cup are preferably provided with a device, preferably a hook that enables one to attach the combined net-piece with cup to the perforated side-walls of the baskets in automatic tissue processors so that the net remains in the vertical position.

BRIEF DESCRIPTION OF THE DRAWING:

FIGS. 1A–1D demonstrates the principle of the cytological paraffination and specimen enrichment method.

FIGS. 2A–2E shows details of the preferred cup and net-piece.

DETAILED DESCRIPTION OF THE PREFERRED EMBODIMENTS

FIG. 1 shows the principle of the combined paraffination and enrichment method for cytological specimens. The sedimented cytological specimen 1, preferably fixed or postfixed in formalin or some other preferably non-coagulating fixative, is poured or transferred by a pipette into the cup 2, preferably having the shape of a frustrum of a cone the large base of which forms an upper open aperture (FIG. 1A). The aperture is closed by a fine-meshed net 3 which prevents the specimen from escaping but has a hydraulic conductance high enough to permit exchange of processing fluids when the net is kept in a vertical position, and the angle between the bottom of the cup and its side-walls is wide enough to promote a pressure on the net depending mainly on differences in density of the fluids in- and outside the cup (FIG. 1B). The net is preferably attached to a net-piece 4 in FIGS. 2 B–D that can be labelled. After processing the cup containing the specimen in melted paraffine is turned in a vertical position onto a hot plate and the specimen enriches by sedimentation to form a layer covering the bottom of the cup (FIG. 1C), preferably after the net has been gently tapped upon, pierced using a warm scalpel and the specimen has been gently mixed to ensure its even distribution (not shown in the Figure). Visible fragments sedimentate in a second or two, smaller ones according to Stokes' law more slowly but from a practical point of view 10 seconds have proved to ensure complete sedimentation. Also centrifugation of the specimen in the melted paraffin may be considered. After transfer of the cup to a cold plate the paraffin hardens and becomes fixed to the net-piece (not shown in FIG. 1) and the net-piece-paraffin cone is twisted off the cup, inverted and the specimen included in a top layer of the cone (FIG. 1D) is cut on a microtome.

FIG. 2 shows in natural size details of the preferred embodiment of the cup (A) and the net-piece (B-E) used for enrichment and paraffination of cytological specimens. The cup, of which FIG. 2A shows a side-view, is preferably made of a heat-conducting and non-corrosive metal. Thin walls would facilitate conduction of heat but make it difficult to make the angle between the inner surface of the side-walls and the upper surface of the cup sharp enough to prevent from entering the space between the net-piece and the cup. If plastic is used the bottom part of the cup can be constructed so that it can be torn off, making the twisting-off of the paraffin cone unnecessary. The shape and dimensions of the cup can vary provided that the angle between the bottom and side-walls is wide enough (>105°) to promote exchange of the processing fluids. In the preferred embodiment the cup has the shape of a frustrum of a cone, the radius of the upper open aperture being 9 mm and that of the bottom 4 mm, the depth being 13 mm. These specific dimensions give an angle between the bottom and its side-walls of 111°, a compromise between the theoretical arguments presented above. Cups with smaller and above all larger bottom areas require consideration of the angle between the bottom and the side-walls. The upper part of the cup is provided with an encircling ledge 2', the upper part of which mates the corresponding indentation 5' in the net-piece 4, the lower edge fitting the arms of a spring that clamps the cup to the net-piece.

The net-piece 4 according to the invention (FIG. 2. B top view, C longitudinal view, D bottom view, and E cross section with the cup properly attached thereto) is preferably made of plastic and it is provided with a central hole 5 covered by the net that preferably is welded into or glued to it. The essentially rectangular net-piece preferably has outer dimensions fitting the jaws of a microtome. The narrowest part of the central hole 5 is covered by the net 3 and has a radius equalling that of the upper aperture of the cup (2E). The angle between the net and the sidewalls of the cone-shaped hole 5" above the net (FIGS. 2C and E), as well as the angle between the bottom of the cup and its sidewalls, has to be wide to enhance fluid exchange during processing. After the net has been cut open at embedding and while the paraffin at the bottom of the cup is hardening the conical hole 5" is filled with melted paraffin that helps to secure the paraffin cone to the net-piece that will be clamped to the jaws of the microtome when the specimen is sectioned. Beneath the net, the hole 5 the net-piece is provided with an indentation 5' into which the ledge 2' of the cup fits in a mating fashion. The net-piece can be clamped to the cup, preferably using a separate spring or pincers rather than hooks or other devices on the net-piece that can be snapped to the cup. The net could also be attached to the cup by a closing ring.

As outlined above, the method is based on the fact that the net, though preventing the specimen from escaping, has a hydraulic conductance high enough to make possible proper exchange of processing fluids. Such fluid exchange requires not only consideration of the hydraulic conductance of the net but also of the pressure that promote fluid exchange, a factor that has influenced both the vertical position of the net during processing and the angle between the bottom of the preferably conical cup, and its sidewalls and the sidewalls of the upper aperture of the net-piece.

The method described in the invention provides a number of advantages. Even small cell clusters in cytological specimens are enriched and paraffinized without being handled roughly and they can be cut on a microtome and studied by all the methods that are available for histological specimens embedded in paraffin. The specimens are enriched onto so small a section area that no screening is required before a final report is given by a pathologist. In the laboratory the method has proved to be very valuable for fine needle aspiration, brush and similar specimens.

What claimed is:

1. A method for processing cytological specimens comprising:
    inserting the specimens to be processed into a cup-shaped receptacle having a closed bottom part and closed sidewalls, the closed sidewalls having an upper edge which defines an upper aperture in the receptacle having an area larger than an area of the bottom part, the sidewalls forming an obtuse angle of about 105° to about 135° with the bottom part, the aperture being covered with a perforated membrane for retaining the cytological specimens, wherein the membrane is a mesh having a mesh size up to 80 microns;
    inserting the receptacle with specimens in a tissue processing apparatus containing processing fluids with the perforated membrane in a vertical position so as to allow an exchange of processing fluids through the membrane and the introduction of paraffin;
    after processing and removal from the processing apparatus, the receptacle being turned so that the perforated membrane is in a horizontal position and directed upwards, thus permitting the enrichment of the specimens by sedimentation to form an enriched layer at the receptacle bottom; and
    after allowing to harden to form a paraffin block with the enriched layer at the bottom, the block being removed from the receptacle for histological examination.

2. The method of claim 1, wherein the receptacle is of frustoconical shape.

3. The method of claim 2, wherein the angle between the sidewalls and the bottom part of the receptacle is between about 105° and about 120°.

4. The method of claim 1, wherein the angle between the sidewalls and the bottom part of the receptacle is between about 105° and about 120°.

5. The method of any one of claims 1, 2, 3 and 4, wherein the membrane has a mesh size of between about 10 and about 80 μm.

6. The method of claim 5, wherein the mesh size is between about 15 and about 35 μm.

7. The method of claim 6, wherein the mesh size is about 20 μm.

8. The method of claim 1, wherein the receptacle includes a means for attaching the membrane to the receptacle, the attaching means comprising a socket positioned at the upper edge of the receptacle and having an opening which mates the aperture in the receptacle and the membrane is incorporated in the opening, and wherein the socket after processing and paraffination of the specimens and removal of the receptacle forms a support for the solidified paraffin block when it is sectioned using a microtome.

9. The method of claim 8, wherein the receptacle has ridges on its outer sidewalls and the socket is attached to the receptacle by means for engaging the ridges.

10. The method of claim 8, wherein the opening of the socket has sidewalls above the membrane which form an angle with the membrane which is bigger than the angle between the sidewalls and the bottom part of the receptacle.

11. The method of claim 1, wherein the receptacle is made of plastic and has a removable plastic bottom part.

* * * * *

UNITED STATES PATENT AND TRADEMARK OFFICE
CERTIFICATE OF CORRECTION

PATENT NO. : 5,312,758
DATED : May 17, 1994
INVENTOR(S) : Johan E. W. Ahlqvist

It is certified that error appears in the above-indentified patent and that said Letters Patent is hereby corrected as shown below:

Col. 6, line 11 - delete "demonstrates" and substitute
  -- is a series of schematic views which demonstrate --.
Col. 6, line 13 - delete "shows" and substitute -- is a series of schematic views which show --. .
Col. 6, line 61 - after "prevent" insert -- specimens --.

Signed and Sealed this

Sixth Day of September, 1994

Attest:

BRUCE LEHMAN

Attesting Officer

Commissioner of Patents and Trademarks